US011693003B2

(12) United States Patent
Miossec et al.

(10) Patent No.: US 11,693,003 B2
(45) Date of Patent: Jul. 4, 2023

(54) ANTI-IL17A AUTOANTIBODIES FOR TREATING OR REDUCING THE LIKELIHOOD OF OCCURRENCE OF BONE DESTRUCTION ASSOCIATED WITH A CHRONIC AUTOIMMUNE OR INFLAMMATORY DISEASE

(71) Applicants: Hospices Civil de Lyon, Lyons (FR); Universite Claude Bernard Lyon 1, Villeurbanne (FR); Dendritics, Lyons (FR)

(72) Inventors: Pierre Miossec, Bron (FR); Ndieme Thiam, Claix (FR); Jean-Jacques Pin, Saint Bonnet de Mure (FR)

(73) Assignees: Hospices Civil de Lyon, Lyons (FR); Universite Claude Bernard Lyon 1, Villeurbanne (FR); Eurobio Scientific, Courtaboeuf (FR)

( * ) Notice: Subject to any disclaimer, the term of this patent is extended or adjusted under 35 U.S.C. 154(b) by 110 days.

(21) Appl. No.: 16/095,967

(22) PCT Filed: Apr. 24, 2017

(86) PCT No.: PCT/EP2017/059638
§ 371 (c)(1),
(2) Date: Oct. 24, 2018

(87) PCT Pub. No.: WO2017/186631
PCT Pub. Date: Nov. 2, 2017

(65) Prior Publication Data
US 2019/0137489 A1 May 9, 2019

(30) Foreign Application Priority Data
Apr. 25, 2016 (FR) .................... 16 53646

(51) Int. Cl.
*G01N 33/53* (2006.01)
*G01N 33/564* (2006.01)
*C07K 16/24* (2006.01)
*G01N 33/68* (2006.01)

(52) U.S. Cl.
CPC ......... *G01N 33/564* (2013.01); *C07K 16/244* (2013.01); *G01N 33/6863* (2013.01); *G01N 2333/54* (2013.01); *G01N 2800/102* (2013.01); *G01N 2800/52* (2013.01)

(58) Field of Classification Search
CPC ........... G01N 33/564; G01N 2800/102; G01N 2800/52
See application file for complete search history.

(56) References Cited

U.S. PATENT DOCUMENTS

2014/0363422 A1   12/2014   Hayday et al.

FOREIGN PATENT DOCUMENTS

WO   2015186106 A1   12/2015

OTHER PUBLICATIONS

Puel et al. Autoantibodies against IL-17A, IL-17F, and IL-22 in patients with chronic mucocutaneous candidiasis and autoimmune polyendocrine syndrome type I. J Exp Med. Feb. 15, 2010;207(2):291-7.*
Genovese et al.; "A Phase ## Randomized Study of Subcutaneous Ixekizumab, an Anti-Interleukin-17 Monoclonal Antibody, in Rheumatoid Arthritis Patients Who Were Naive to Biologic Agents or Had an Inadequate Response to Tumor Necrosis Factor Inhibitors"; Arthritis & Rheumatology, vol. 66, No. 7, Jul. 2014, pp. 1693-1704.
Heuber et al.; "Effects of AIN457, a Fully Human Antibody to Interleukin-17A, on Psoriasis, Rheumatoid Arthritis, and Uveitis"; Science Translational Medicine, vol. 2, No. 52, Oct. 2010, pp. 1-9.
Jouvenne et al.; "High Levels of Neutralizing Autoantibodies Against IL-1α are Associated with a Better Prognosis n Chronic Polyarthritis: a Follow-Up Study"; Scandinavian Journal of Immunology, vol. 46, No. 4, Oct. 1997, pp. 413-418.
Miossec; "Anti-interleukin 1α autoantibodies"; Ann. Rheum. Dis., vol. 61, No. 7, Oct. 1997, pp. 577-579.
Ndongo-Thiam et al.; "A cell-based bioassay for ciiculating bioactive IL-17: application to destruction in rheumatoid arthritis"; Ann. Rheum. Dis., vol. 74, No. 8, Aug. 2015, pp. 1629-1631.
Ndongo-Thiam et al.; "Negative associated between autoantibodies against IL-17, IL-17/anti-IL-17 antibody immune complexes and destruction in rheumatoid arthritis"; Ann. Rheum. Dis.; vol. 75, No. 7, Apr. 29, 2016, pp. 1420-1422.

* cited by examiner

*Primary Examiner* — Dong Jiang
(74) *Attorney, Agent, or Firm* — WC&F IP

(57) ABSTRACT

The present invention relates to an in vitro method for evaluating the prognosis of an autoimmune or chronic inflammatory disease in an individual, comprising the following steps: a) determining (i) the level of an anti-IL-17 autoantibody and/or (ii) the level of an [IL-17/anti-IL-17 autoantibody] complex in a biological sample of the individual, and b) comparing the level of autoantibody and/or of complex determined in step a) with a reference value, the comparison being indicative of the prognosis of an autoimmune or chronic inflammatory disease in said individual.

5 Claims, 5 Drawing Sheets

Figure 1A:
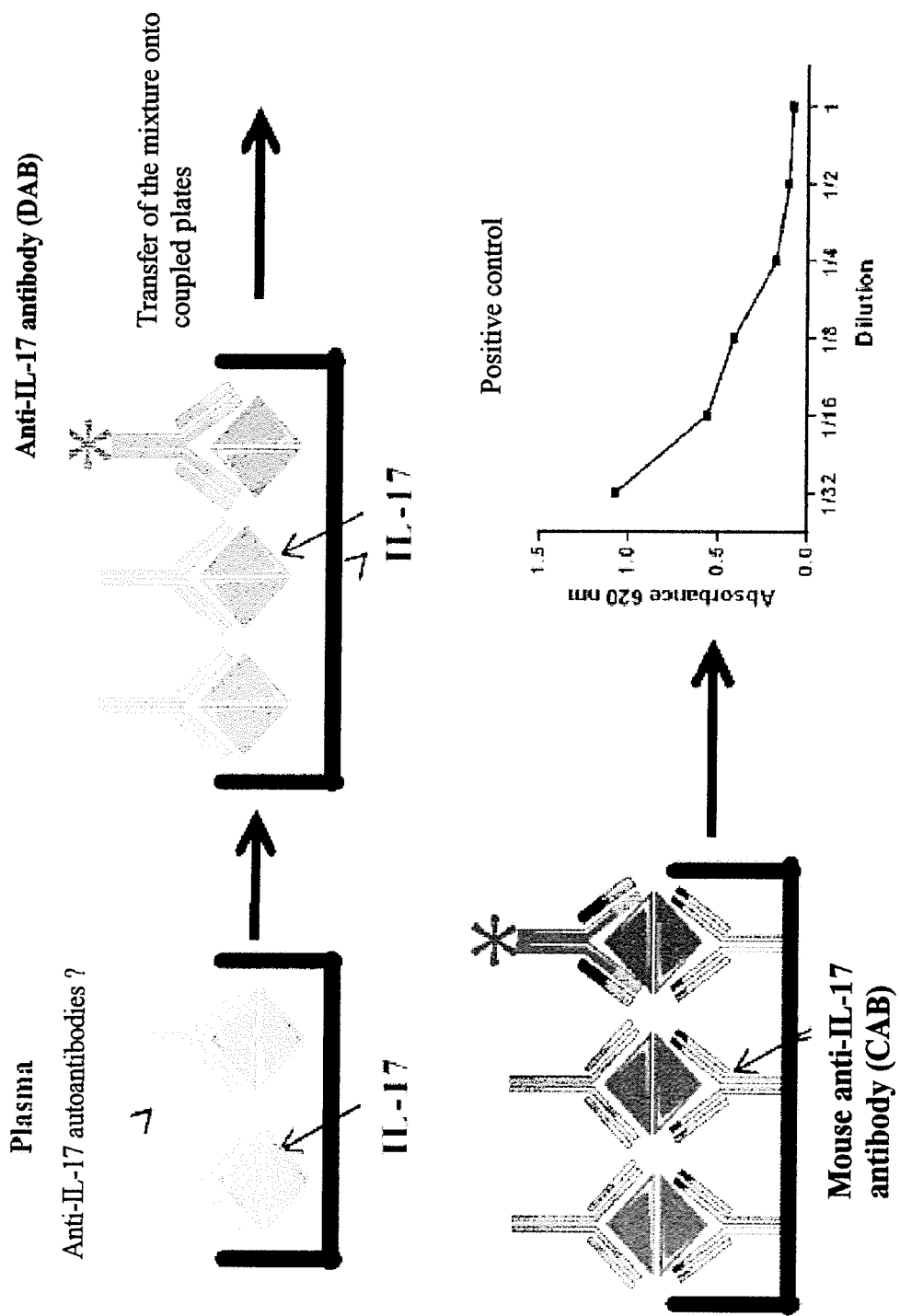

ANTI-IL17A AUTOANTIBODIES FOR TREATING OR REDUCING THE LIKELIHOOD OF OCCURRENCE OF BONE DESTRUCTION ASSOCIATED WITH A CHRONIC AUTOIMMUNE OR INFLAMMATORY DISEASE

FIELD OF THE INVENTION

The present invention relates to the identification of biological markers for a chronic autoimmune or inflammatory disease in an individual, and most particularly for rheumatoid arthritis (RA). The invention describes a method for determining the level of these new biomarkers, new antibodies and also the therapeutic, diagnostic or prognostic applications thereof.

PRIOR ART

Autoimmune diseases are generally characterized by the triggering of an immune reaction, which results in an inflammatory reaction, against substances and/or tissues normally present in the individual. They are often, but not systematically, revealed by the detection of autoantibodies directed against "self" antigens.

These chronic autoimmune and inflammatory diseases are heterogeneous pathological conditions, for which there is great variability in terms of phenotypes and treatment responses. Thus, the prognosis of these chronic autoimmune and inflammatory diseases is liable to vary considerably within individuals who are nevertheless considered to be suffering from the same pathological condition.

In particular, rheumatoid arthritis is a chronic inflammatory degenerative disease characterized by involvement of the joints, which is often bilateral and symmetrical, and which progresses via attacks toward deformation and destruction of the affected joints. Symptomatic treatment makes use of nonsteroidal anti-inflammatories and corticosteroids. Nowadays, methotrexate is the reference treatment. "Fundamental" treatments for the disease are actively sought, in particular by identification of the cytokines and cells involved in the inflammatory process of the disease. These treatments call for specific inhibitors of the cytokines and cells involved. Mention may in particular be made of Etanercept® and Infliximab®, which are TNF (Tumor Necrosis Factor) inhibitors. Other treatments use interleukin antagonists such as IL-1 inhibitors (Anakinra®), IL-6 receptor inhibitors (MrA®) and anti-CD20s (Rituximab®). These compounds reduce the inflammation and slow down the progression of the disease.

Nevertheless, a strong variation in response is observed between patients suffering from rheumatoid arthritis, who do not respond similarly to these treatments. It is in particular estimated that up to 30% of patients do not respond at all to the biotherapies listed above.

It has been shown that IL-17 plays a major role in inflammatory diseases, autoimmune diseases, certain infections and cancer. Thus, this cytokine is now considered to be a potential therapeutic target for many diseases (Miossec, Kom, and Kuchroo, 2009, NEJM). The major two forms of this cytokine are called IL-17A and IL-17F. IL-17A induces the production of numerous cytokines and chemokines, such as IL-6, G-CSF, IL-1β and IL-8. In rheumatoid arthritis, IL-17 is present at the inflammation sites and acts by amplifying the inflammatory effects of other compounds such as TNF, which makes it a significant player in the physiology of the disease. However, the circulating levels of IL-17 in the plasma of patients are often very low, and very great heterogeneity in the circulating levels of IL-17 is observed between patients.

IL-17A inhibitors, in particular antibodies, have been proposed for the treatment of inflammatory diseases, and various clinical trials are ongoing (Miossec and Kolls, 2012). The first results obtained indicate that it is difficult to predict what the response of patients will be to these treatments, since there is a very strong individual variation.

In some patients, the role of IL-17 in the inflammatory phenomenon is considerable, whereas in other patients it is very weak. A major effort must now be brought to the preselection of patients whose inflammatory condition is directly dependent on IL-17, since it is these patients who would benefit from this type of treatment.

WO 2015/186106 teaches in particular in vitro methods using the level of functional IL-17 (IPDL) as a biomarker, for determining the chances of response of a patient, suffering from a chronic inflammatory condition, to the administration of an anti-IL-17 antibody.

Thus, there remains a need to identify new markers for these chronic autoimmune and inflammatory diseases, and in particular for rheumatoid arthritis. There also remains a need to identify new methods and tools for the diagnosis, prognosis and/or treatment of these chronic autoimmune and inflammatory diseases.

SUMMARY OF THE INVENTION

The present invention describes a biomarker for chronic autoimmune or inflammatory diseases, based on the detection, in a biological sample, of an anti-IL-17 autoantibody, which may be determined either from the viewpoint of a total level, or in a complex with interleukin-17.

The present invention thus relates to an in vitro method for evaluating the prognosis of a chronic autoimmune or inflammatory disease in an individual, comprising the following steps:

a) determining (i) the level of an anti-IL-17 autoantibody and/or (ii) the level of an [IL-17/anti-IL-17 autoantibody] complex in a biological sample from said individual, and b) comparing the level of autoantibody and/or of complex determined in step a) with a reference value, said comparison being indicative of the prognosis of a chronic autoimmune or inflammatory disease in said individual.

Among these chronic autoimmune or inflammatory diseases, rheumatoid arthritis (RA) is most particularly taken into consideration.

The preceding methods also make it possible to identify particular populations of individuals, such as particular populations of individuals suffering from rheumatoid arthritis, for whom it is possible to administer an IL-17-inhibiting active ingredient.

The knowledge of this new biomarker allows in particular the following diagnostic and/or prognostic applications:

(i) determining the risk of severity, in particular of bone destruction, in an individual suffering from a chronic autoimmune or inflammatory disease, and in particular from rheumatoid arthritis;

(ii) determining the chances of response, of an individual suffering from a chronic autoimmune or inflammatory disease, to a treatment comprising the administration of an IL-17-inhibiting active ingredient, such as an anti-IL-17 antibody;

(iii) determining the efficacy of a treatment or of a prevention of bone destruction in an individual suffering from a chronic autoimmune or inflammatory disease, said treatment or said prevention consisting of the administration of an IL-17-inhibiting active ingredient, such as an anti-IL-17 antibody.

In particular, the present invention describes an in vitro method for selecting antibodies for treating (i) a chronic autoimmune or inflammatory disease, and/or (ii) bone destruction associated with said disease, comprising the following steps:

a) determining the presence (i) of an anti-IL-17 autoantibody and/or (ii) of an [IL-17/anti-IL-17 autoantibody] complex in a biological sample from an individual evaluated by said in vitro method or as claimed in claim 1;

b) selecting an anti-IL-17 autoantibody or a cell producing an anti-IL-17 autoantibody from a biological sample from said individual; said autoantibody being capable of treating said disease, and/or said bone destruction.

The present invention also relates to an in vitro method for distinguishing destructive rheumatoid arthritis from non-destructive rheumatoid arthritis in an individual, comprising the following steps:

a) determining (i) the level of an anti-IL-17 autoantibody and/or (ii) the level of an [IL-17/anti-IL-17 autoantibody] complex in a biological sample from said individual, and b) comparing the level of autoantibody and/or of complex determined in step a) with a reference value, said comparison being indicative of destructive or non-destructive rheumatoid arthritis in said individual.

The present invention also relates to an isolated anti-IL-17 antibody for the treatment or prevention (i) of destructive rheumatoid arthritis and/or (ii) of rheumatoid arthritis in an individual not producing anti-IL-17 autoantibody, or of bone destruction associated with either one of groups (i) and (ii).

The present invention also relates to the use of an isolated anti-IL-17 antibody for preparing a medicament for the treatment or prevention (i) of destructive rheumatoid arthritis and/or (ii) of rheumatoid arthritis in an individual not producing anti-IL-17 autoantibodies, or of bone destruction associated with either one of groups (i) and (ii).

The present invention also relates to an isolated human anti-IL-17 antibody obtained from a biological sample from an individual suffering from rheumatoid arthritis and producing anti-IL-17 autoantibodies.

Said biological sample may comprise, or consist of, a cell which produces said anti-IL-17 antibody.

FIGURE LEGENDS

Figure 1B:
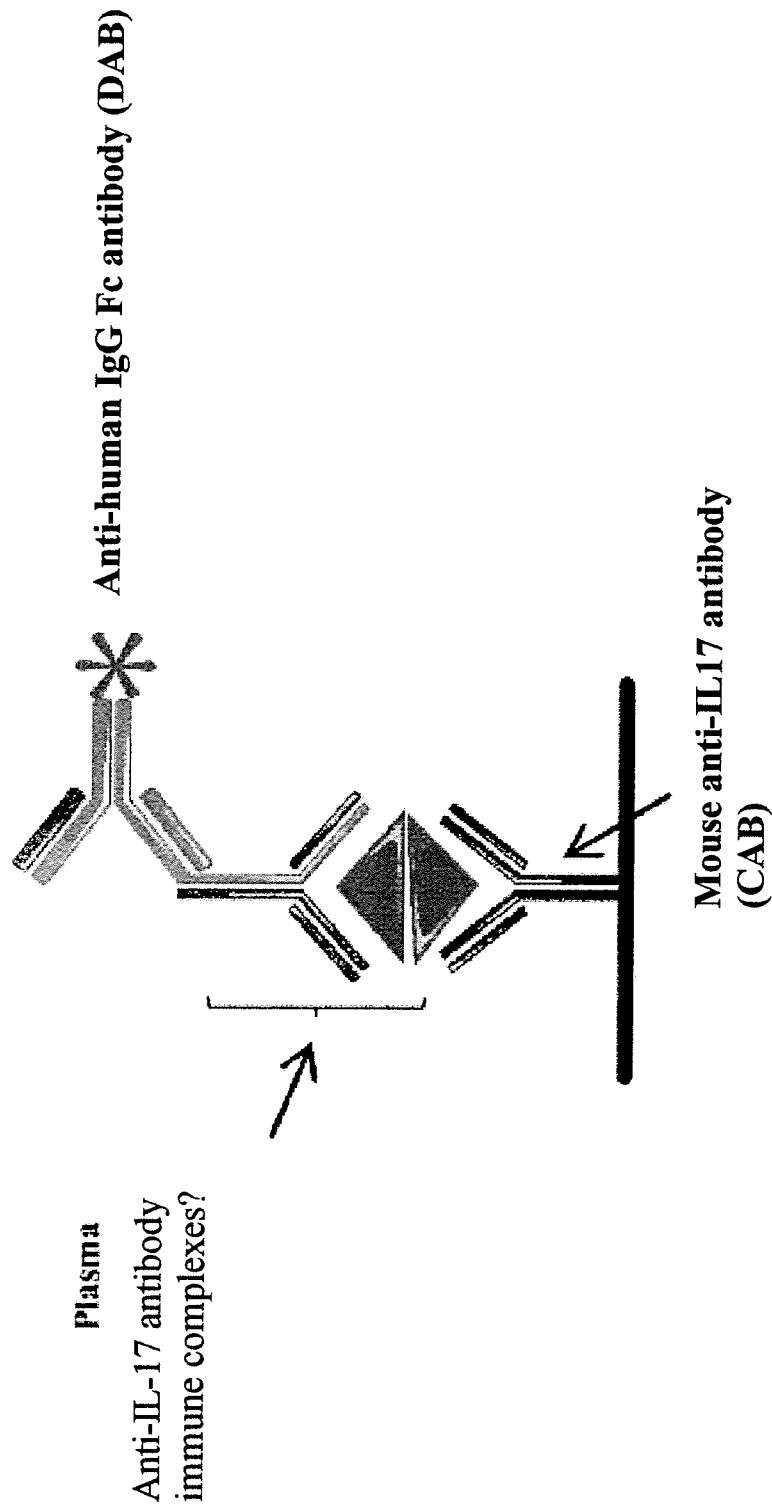

FIG. 1: Principle of detection of anti-IL-17 autoantibodies and of IL-17/anti-IL-17 antibody complexes The anti-IL-17 autoantibodies are detected in the plasma by means of a competitive ELISA assay (A). The IL-17 and the plasma are combined so as to promote binding of the IL-17 and of the anti-IL-17 antibody. Anti-IL-17 and irrelevant antibodies were used, respectively, as positive and negative controls. An anti-IL-17 detection antibody was then added. The mixture was then transferred to plates comprising the anti-human IL-17 capture antibody.

The [IL-17/anti-IL-17 autoantibody] complexes are detected in the plasma by means of an indirect ELISA assay (B). Plasma preincubated with horse serum is added to a 96-well plate comprising the anti-IL-17 capture antibody. The positive-control immune complex (IC) was formed in vitro from 500 ng of IL-17 and 5 µg/ml of human anti-human-IL1-17 antibody. A goat anti-human IgG Fc fragment antibody (anti-human IgG Fc) conjugated to peroxidase was used for the visualization.

Figure 2A:
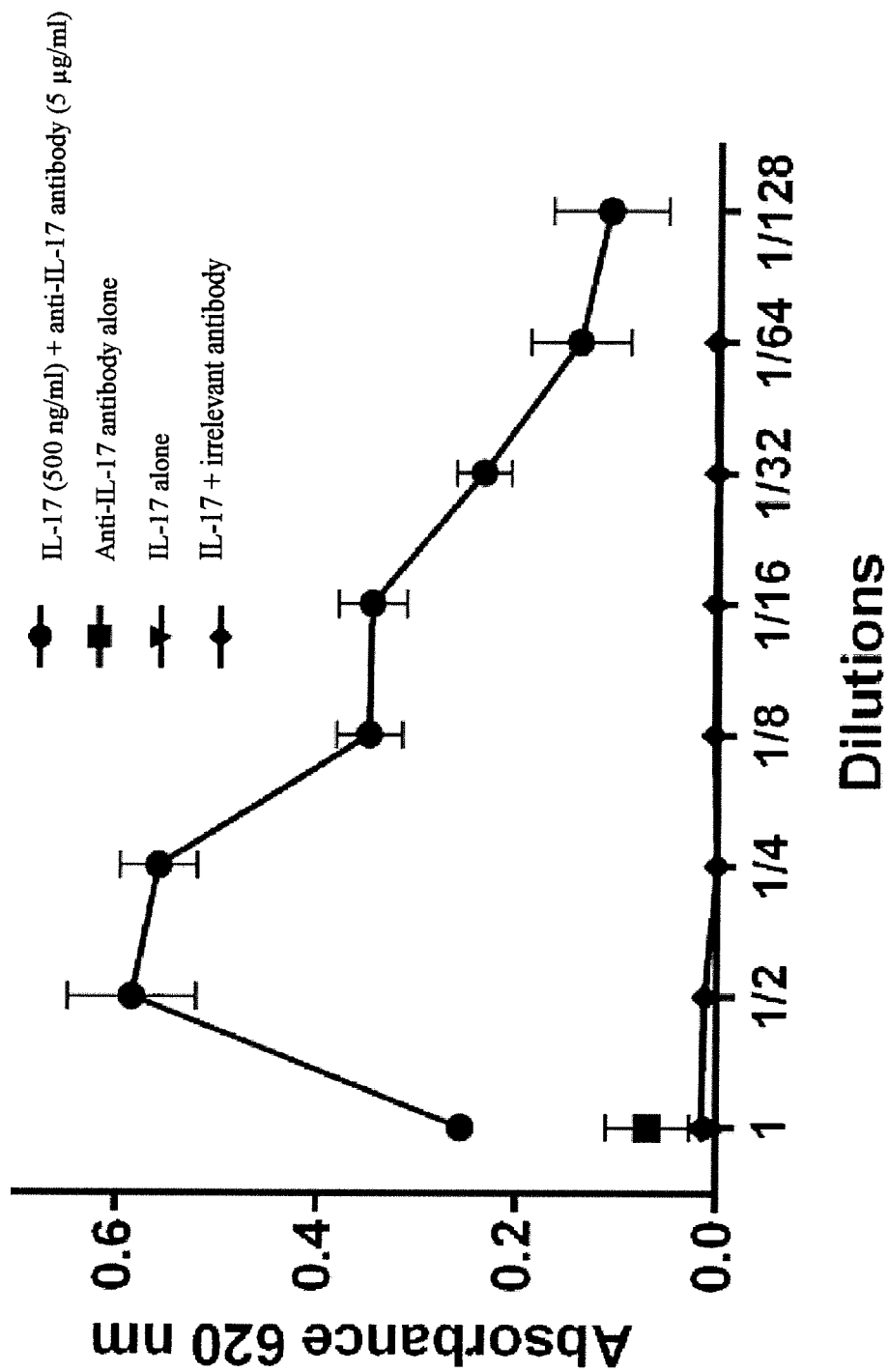
Figure 2B:
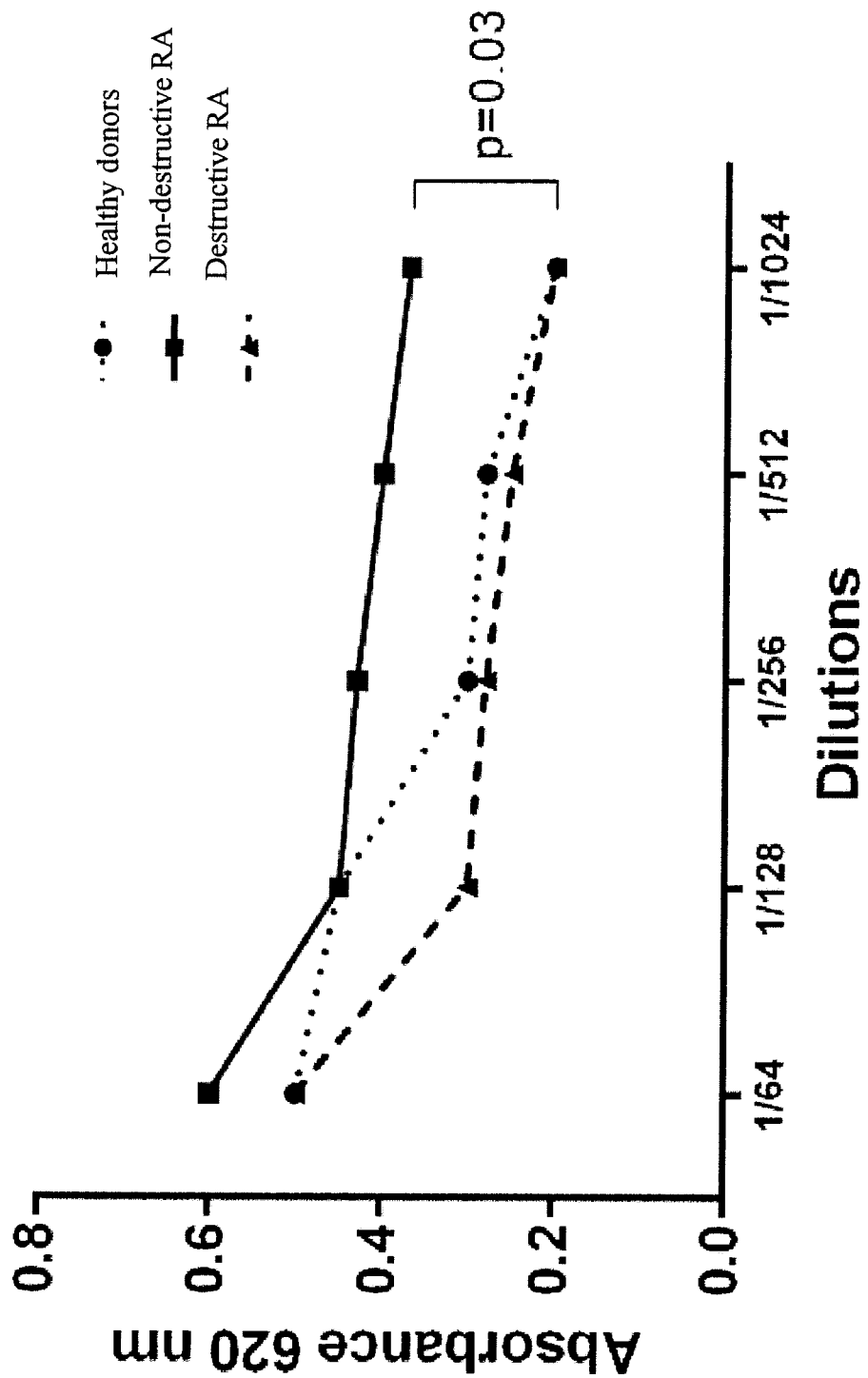
Figure 2C:
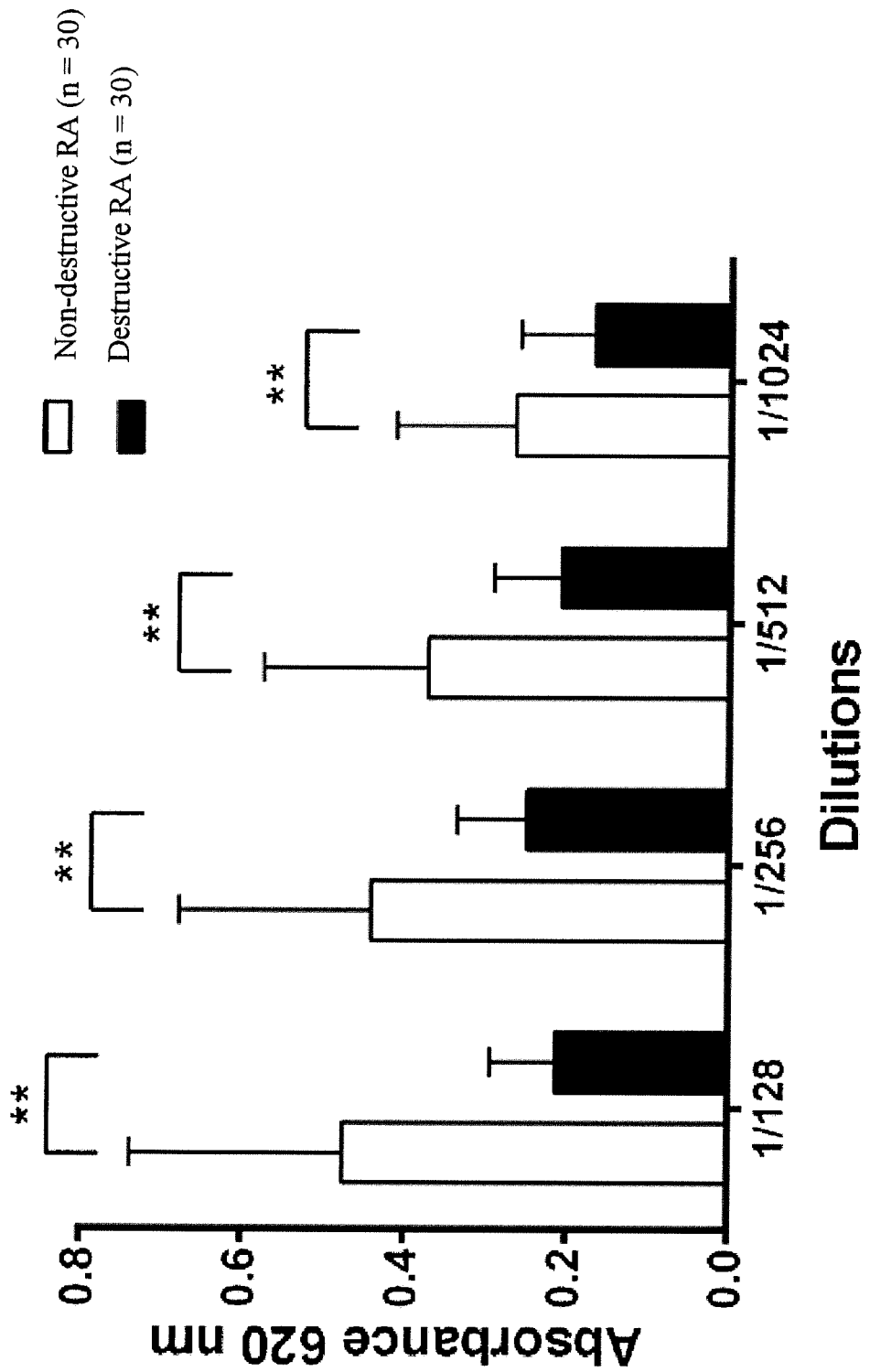

FIG. 2: Detection of IL-17/anti-IL-17 antibody complexes in the plasma of patients suffering from destructive and non-destructive rheumatoid arthritis, compared with healthy donors An eight-point standard curve was determined from serial (2-fold) dilutions and tested with the positive control formed in vitro from 500 ng of IL-17 and 5 µg/ml of human anti-human-IL1-17 antibody (A).

The immune complexes (IC) are detected in the plasma of 30 healthy donors and of 60 patients suffering from rheumatoid arthritis (RA) with or without bone destruction. For each plasma sample, a standard curve of serial (2-fold) dilutions was tested to determine the immune complex titers (B).

The mean level of [IL-17/anti-IL-17 autoantibody] immune complexes in the non-destructive RA compared with destructive RA groups are represented (C). The Mann-Whitney test shows a statistically significant (*<0.05; ***<0.001) difference (p value). The error bars represent the standard deviation.

DETAILED DESCRIPTION OF THE INVENTION

Surprisingly and unexpectedly, the inventors have identified the presence of anti-IL-17 autoantibodies in individuals suffering from rheumatoid arthritis.

Also surprisingly, the inventors have shown that the production of anti-IL-17 autoantibodies and/or of [IL-17/anti-IL-17 autoantibody] immune complexes is more common in individuals suffering from non-destructive rheumatoid arthritis than those suffering from destructive rheumatoid arthritis.

This negative relationship between the presence of anti-IL-17 autoantibodies and the bone destruction phenomenon in this chronic autoimmune and inflammatory disease suggests that these autoantibodies and [IL-17/anti-IL-17 autoantibody] complexes protect against bone destruction, by neutralizing all or part of the function of interleukin 17 (IL-17).

IL-17 or IL17 denotes the interleukin-17 as identified in 1993 by the team of Rouvier et al. It was renamed IL-17A after the identification of new identified members of the family, called IL-17B to IL-17F. IL-17 is a homodimeric glycoprotein of 155 amino acids, with a weight of 35 kDa. IL-17 is secreted by CD4+ and CD8+ lymphocytes and is involved in the coordination of local inflammation of tissues, in particular via the induction of secretion of cytokines which are pro-inflammatory and which induce neutrophil mobilization (Kolls and Linden, 2004).

Indeed, IL-17 induces the secretion of pro-inflammatory factors by its numerous targets cells, each target cell type being specialized in the production and secretion of one or more cytokines or chemokines.

The present invention relates most particularly to IL-17A, but may also be applied to other members of the family: IL-17B, IL-17C, IL-17D, IL-17E and in particular IL-17F which exhibits the highest degree of sequence identity with IL-17A. By analogy, the antibodies, anti-IL-17A autoantibodies, and complexes comprising said autoantibodies are most particularly taken into consideration, although those specifically directed against the other members are also relevant from a clinical (diagnostic, prognostic and/or therapeutic) point of view.

Admittedly, it was known that chronic autoimmune diseases could be characterized by the presence of autoantibodies. It was also known that interleukin 17 (IL-17) could constitute a therapeutic target regarding an increasing number of inflammatory diseases.

Thus, clinical trials for the treatment of rheumatoid arthritis using anti-IL-17 antibodies have already been reported, in particular by Hueber et al. (Sci Transl Med. 2010; 2: 52ra72) and Genovese et al. (Arthritis Rheumatol. 2014; 66: 1693-1704). However, the results resulting from these clinical trials are heterogeneous.

Without wishing to be bound by theory, the inventors are of the opinion that this heterogeneity is linked to the presence, at variable levels, of anti-IL-17 autoantibodies and/or of [IL-17/anti-IL-17 autoantibody] immune complexes.

In particular, the results obtained (see examples) on biological samples from patients suggest that, in non-destructive rheumatoid arthritis, these anti-IL-17 autoantibodies are present in excess and bind interleukin IL-17 to form further [IL-17/anti-IL-17 autoantibody] complexes; the consequence observed is thus a decrease or even an absence of detectable levels of free bioactive IL-17.

The detection of anti-IL-17 autoantibodies and/or of [IL-17/anti-IL-17 autoantibody] immune complexes in these individuals therefore represents a biomarker of interest for predicting the prognosis of these chronic autoimmune and inflammatory diseases, in particular for predicting bone destruction associated with these diseases, but also for predicting a response to a treatment in this context.

The term "bone destruction" is intended to denote a gradual disappearance of the bone tissue due to the chronic inflammatory state of the patient.

The term "destructive rheumatoid arthritis" is intended to denote the occurrence of rheumatoid arthritis in an individual, for whom bone destruction is associated. Conversely, the term "non-destructive rheumatoid arthritis" is intended to denote the occurrence of rheumatoid arthritis in a patient, for whom bone destruction is not associated.

With regard to the experimental data, "non-destructive rheumatoid arthritis" is statistically liable to correspond to rheumatoid arthritis associated with the production of anti-IL-17 autoantibodies.

Conversely, "destructive rheumatoid arthritis" is statistically liable to correspond to rheumatoid arthritis not associated with the production of anti-IL-17 autoantibodies, or for which the production of anti-IL-17 autoantibodies is insufficient.

The occurrence of destructive or non-destructive rheumatoid arthritis may also be determined on the basis of the Larsen score, and most particularly the wrist Larsen score. A Larsen score above 2 is generally considered to be characteristic of destructive rheumatoid arthritis. A Larsen score between 0 and 1 generally corresponds to non-destructive rheumatoid arthritis. The significance and the determination of a Larsen score, in particular a wrist Larsen score, is part of the general knowledge of those skilled in the art.

The expression "determination of the production of anti-IL-17 autoantibodies" is in particular intended to denote (i) the level of an anti-IL-17 autoantibody and/or (ii) the level of an [IL-17/anti-IL-17 autoantibody] complex.

The term "antibodies" is herein used in its most general sense, and covers specifically monoclonal antibodies (including complete monoclonal antibodies), polyclonal antibodies (for example bispecific antibodies), and antibody fragments provided that they exhibit the desired biological activity.

The term "antibody fragment" denotes antibody fragments comprising a part of a complete antibody, generally the part responsible for binding to the antigen or its variable domain. Examples of antibody fragments include the Fab, Fab', F(ab')$_2$ and Fv fragments; diabodies; linear antibodies; single-chain antibodies; and multispecific antibodies formed from antibody fragments.

The term "autoantibody" denotes an antibody produced by the immune system of the host himself or herself and directed against one or more of his or her proteins.

The term "individual" encompasses any human or non-human (preferably human) individual who may develop a chronic autoimmune or inflammatory disease.

According to a first embodiment, the invention relates to an in vitro method for evaluating the prognosis of a chronic autoimmune or inflammatory disease in an individual, comprising the following steps:

a) determining (i) the level of an anti-IL-17 autoantibody and/or (ii) the level of an [IL-17/anti-IL-17 autoantibody] complex in a biological sample from said individual, and b) comparing the level of autoantibody and/or of complex determined in step a) with a reference value, said comparison being indicative of the prognosis of a chronic autoimmune or inflammatory disease in said individual.

In particular, the chronic autoimmune or inflammatory disease is chosen from: rheumatoid arthritis, psoriasis, psoriatic arthritis, ankylosing spondylitis, multiple sclerosis, lupus, Crohn's disease, vasculitis (including involvement of associated organs), an associated cardiovascular disease, myositis, hepatitis, inflammatory and autoimmune nephropathy, neutrophilic dermatosis, Verneuil's disease and uveitis.

Preferably, and as illustrated in the examples, the chronic autoimmune or inflammatory disease is rheumatoid arthritis (RA). Thus, rheumatoid arthritis may be:
  destructive rheumatoid arthritis;
  non-destructive rheumatoid arthritis;
  rheumatoid arthritis in an individual producing anti-IL-17 autoantibodies; or
  rheumatoid arthritis in an individual not producing anti-IL-17 autoantibodies.

More specifically, the in vitro method as defined above may be carried out for (i) determining the risk of bone destruction in an individual suffering from said chronic autoimmune or inflammatory disease; and/or (ii) determining the chances of response, of an individual suffering from said chronic autoimmune or inflammatory disease, to a treatment comprising the administration of an IL-17-inhibiting active ingredient (in particular an anti-IL-17 antibody); and/or (iii) determining the efficacy of a treatment or of a prevention of bone destruction in an individual suffering from said chronic autoimmune or inflammatory disease, said treatment or said prevention consisting of the administration of an IL-17-inhibiting active ingredient (in particular an anti-IL-17 antibody).

Thus, according to these particular embodiments, the comparison in step b) is indicative of said risk of bone destruction, of said chances of response to said treatment, and/or of the efficacy of said treatment or of said prevention of bone destruction.

The invention thus relates to an in vitro method for selecting an individual in whom the presence of anti-IL-17 autoantibodies reflects the presence, in a biological sample (including blood) from said individual, of cells producing this antibody. This presence of cells producing anti-IL-17 autoantibodies enables them to be isolated from said sample, and in particular from a blood sample.

The use of current laboratory techniques then makes it possible to isolate said anti-IL-17 autoantibody, in particular for therapeutic use.

In particular, this in vitro evaluation method may be carried out in an in vitro method for selecting an antibody for treating (i) a chronic autoimmune or inflammatory disease, and/or (ii) bone destruction associated with said disease, comprising the following steps:

a) determining the level (i) of an anti-IL-17 autoantibody and/or (ii) of an [IL-17/anti-IL-17 autoantibody] complex in a biological sample from an individual evaluated according to the methods described above, and/or as claimed in claim 1;

b) selecting an anti-IL-17 autoantibody or a cell producing an anti-IL-17 autoantibody from a biological sample from said individual; said autoantibody being capable of treating said disease and/or said bone destruction.

The biological samples of steps a) and b) of said selection method may be identical or different. The selection step b) may be carried out using any biological sample which may comprise said anti-IL-17 autoantibody or said producer cell, which includes: the serum, the plasma, the blood and the primary or secondary lymphoid organs.

Thus, the invention relates to an in vitro method for selecting antibodies for treating (i) a chronic autoimmune or inflammatory disease, and/or (ii) bone destruction associated with said disease, comprising the following steps:

a) determining the level (i) of an anti-IL-17 autoantibody and/or (ii) of an [IL-17/anti-IL-17 autoantibody] complex in a biological sample from an individual suffering from a chronic autoimmune or inflammatory disease;

b) comparing the level of autoantibody and/or of complex determined in step a) with a reference value;

c) selecting an anti-IL-17 autoantibody or a cell producing an anti-IL-17 autoantibody from a biological sample from said individual; said autoantibody being capable of treating said disease and/or said bone destruction.

In the context of said in vitro antibody selection methods, the biological sample may in particular be from an individual suffering from rheumatoid arthritis, and preferably suffering from non-destructive rheumatoid arthritis.

According to a second embodiment, the invention relates to an in vitro method for distinguishing destructive rheumatoid arthritis (RA) from non-destructive rheumatoid arthritis in an individual, comprising the following steps:

a) determining (i) the level of an anti-IL-17 autoantibody and/or (ii) the level of an [IL-17/anti-IL-17 autoantibody] complex in a biological sample from said individual, and b) comparing the level of autoantibody and/or of complex determined in step a) with a reference value, said comparison being indicative of destructive or non-destructive rheumatoid arthritis (RA) in said individual.

According to a third embodiment, the invention relates to an isolated anti-IL-17 antibody, for the treatment or prevention (i) of destructive rheumatoid arthritis and/or (ii) of non-destructive rheumatoid arthritis and/or (iii) of rheumatoid arthritis in an individual producing anti-IL-17 autoantibodies and/or (iv) of rheumatoid arthritis in an individual not producing anti-IL-17 autoantibodies, and/or (v) of bone destruction regarding any one of groups (i) to (iv).

According to a fourth embodiment, the invention relates to an isolated human anti-IL-17 antibody obtained from a biological sample from an individual suffering from rheumatoid arthritis and producing anti-IL-17 autoantibodies.

An isolated anti-IL-17 antibody according to the invention is preferably an antibody isolated using the in vitro selection method of the invention, and/or an antibody isolated from a biological sample from an individual suffering from rheumatoid arthritis, and preferably suffering from non-destructive rheumatoid arthritis.

In particular, said anti-IL-17 antibody may be obtained according to a method comprising the following steps:

a) preparing a composition enriched with lymphocytes producing anti-IL-17 antibody from a sample originating from an individual suffering from rheumatoid arthritis, and preferably suffering from non-destructive rheumatoid arthritis, b) selecting at least one B lymphocyte producing anti-IL-17 antibody, or at least one clone of B lymphocytes producing anti-IL-17 antibody, and c) obtaining said anti-IL-17 antibody.

In some embodiments, the sample from which the composition enriched with lymphocytes producing anti-IL-17 antibody is prepared, in step a), is a sample originating from human blood, which encompasses whole blood and a blood fraction enriched with cells, such as a fraction enriched with peripheral blood mononuclear cells and a fraction enriched with lymphocytes.

Step b) may be carried out according to any technique well known to those skilled in the art.

Step c) may be carried out by culturing the B lymphocyte(s) selected in step b), then purifying the anti-IL-17 antibody thus produced.

Usually, the B lymphocyte(s) selected in step b) are then immortalized in the form of a cell line producing said anti-IL-17 antibody. The cells in the line are then cultured and the anti-IL-17 antibody thus produced is subsequently purified.

In Vitro Methods

For the purposes of carrying out the in vitro methods described above, the term "reference value" is intended to mean a level of anti-IL-17 autoantibody and/or (ii) a level of [IL-17/anti-IL-17 autoantibody] complex determined in individuals/patients suffering from a chronic autoimmune or inflammatory disease, for example rheumatoid arthritis, and in whom the occurrence or non-occurrence of bone destruction is optionally known, or for which a bone destruction phenomenon has, where appropriate, been observed.

In general, said reference value is a mean value measured using a biological sample from a plurality of individuals suffering from the same chronic autoimmune or inflammatory disease, for example rheumatoid arthritis, and in whom the occurrence (or non-occurrence) of bone destruction, or else in whom the production of said levels of anti-IL-17 autoantibody and/or (ii) level of [IL-17/anti-IL-17 autoantibody] complex, is known.

For the purposes of carrying out the methods according to the invention, a mean value determined or measured in patients suffering from a chronic autoimmune or inflammatory disease, for example rheumatoid arthritis, and in whom the occurrence or non-occurrence of bone destruction is observed, may be chosen as "reference value".

In some embodiments of the method, the reference value is a value determined in individuals not exhibiting bone destruction and/or in individuals in whom the chronic autoimmune or inflammatory disease is associated with the production of anti-IL-17 autoantibody and/or of [IL-17/anti-IL-17 autoantibody] complex. In these embodiments, a patient tested according to the method of the invention will be classified as "at reduced or zero risk of bone destruction" when the (i) level of anti-IL-17 antibody and/or (ii) level of [IL-17/anti-IL-17 autoantibody] complex is greater than said reference value.

In some embodiments of the method, the reference value is a value determined in patients exhibiting bone destruction and/or in individuals in whom the chronic autoimmune or inflammatory disease is not associated with the production of anti-IL-17 autoantibody and/or of [IL-17/anti-IL-17 autoantibody] complex.

In these embodiments, a patient tested according to the method of the invention will be classified as "at moderate or high risk of bone destruction" when the (i) level of anti-IL-17 autoantibody and/or (ii) level of [IL-17/anti-IL-17 autoantibody] complex is less than said reference value.

In some embodiments of the method, the reference value is a value determined in one and the same patient, before or after administration of an active ingredient to said patient, or else before or after bringing the biological sample into contact with said active ingredient. This embodiment may advantageously show its value for determining:
  the chances of response, of an individual suffering from said chronic autoimmune or inflammatory disease, to a treatment comprising the administration of an IL-17-inhibiting active ingredient; and/or
  the efficacy of a treatment or of a prevention of bone destruction in an individual suffering from said chronic autoimmune or inflammatory disease, said treatment or said prevention consisting of the administration of an IL-17-inhibiting active ingredient.

The step of administrating an active ingredient, or candidate compound, will be carried out over an appropriate period of time in order to judge the efficacy of said compound, this period of time ranging from one day to several months, and being calculated with regard to the usual periods of time for administrating compounds of this type.

Thus, according to one particular embodiment, the invention relates to an in vitro method for evaluating the prognosis of a chronic autoimmune or inflammatory disease in an individual, for determining:
  the chances of response, of said individual, to a treatment comprising the administration of an IL-17-inhibiting active ingredient; and/or
  the efficacy of a treatment or of a prevention of bone destruction in said individual, said treatment or said prevention consisting of the administration of an IL-17-inhibiting active ingredient; and comprising the following steps:
  a) determining (i) the level of an anti-IL-17 autoantibody and/or (ii) the level of an [IL-17/anti-IL-17 autoantibody] complex in a biological sample from said individual before said administration;
  b) administering said IL-17-inhibiting active ingredient to the individual;
  c) determining (i) the level of an anti-IL-17 autoantibody and/or (ii) the level of an [IL-17/anti-IL-17 autoantibody] complex in a biological sample from said individual after said administration; and
  d) comparing the level of autoantibody and/or of complex determined in steps a) and c) with a reference value, said comparison being indicative of said chances of response to and/or of the efficacy of said treatment or prevention.

It is understood that said IL-17-inhibiting active ingredient (which is preferably an anti-IL-17 antibody) is judged to be efficacious when the value determined in step a) is greater than the value determined in step c).

In other further embodiments, the reference value is a value termed "threshold" or "cut-off", which is determined from (i) values determined in patients "at reduced or zero risk" and (ii) values determined in patients "at moderate or high risk". In these embodiments, a patient tested according to the method of the invention will be classified as "at reduced or zero risk of bone destruction" when the (i) level of anti-IL-17 autoantibody and/or (ii) level of [IL-17/anti-IL-17 autoantibody] complex measured for this patient is greater than the reference value.

A "threshold" or "cut-off" reference value may be easily determined by those skilled in the art using their general knowledge. A "threshold" or "cut-off" reference value may for example be determined as described by Limmathurotsakul et al. (2011, CID, vol. 52: 1024-1028).

It is understood that, for carrying out all these methods, the biological sample has been taken from the individual tested, and that it is a sample of whole blood, plasma, serum, synovial fluid, cerebrospinal fluid, pleural fluid or peritoneal fluid from said individual.

Said in vitro methods may also be carried out on any type of cells capable of producing said autoantibodies, which includes the B lymphocytes from individuals who have a chronic autoimmune or inflammatory disease, for example rheumatoid arthritis.

When the biological sample comprises or consists of cells, these methods will preferably be characterized in that the cells used are primary cultures of cells, in particular of cells taken from the individual from whom the biological sample is tested.

According to one particular embodiment of these in vitro methods, step a) consists in determining the level of an anti-IL-17 autoantibody in said biological sample.

According to another particular embodiment of these in vitro methods, step a) consists in determining the level of an [IL-17/anti-IL-17 autoantibody] complex in said biological sample.

In particular, the biological sample may be chosen from: whole blood, plasma and serum.

According to one preferred embodiment, the anti-IL-17 autoantibody is an anti-IL-17A autoantibody; and the [IL-17/anti-IL-17 autoantibody] complex is an [IL-17A/anti-IL-17A autoantibody] complex.

Thus, the anti-IL-17 autoantibody may preferably be a human autoantibody directed against human interleukin IL-17A.

The determination of the level of an anti-IL-17 autoantibody and/or (ii) the level of an [IL-17/anti-IL-17 autoantibody] complex in a biological sample may be carried out by any test known to those skilled in the art. Non-exhaustively, tests for determining autoantibodies are referenced in Aggarwal et al (Best Practice & Research Clinical Rheumatology 28 (2014) 907-920).

For example, the determination of the level of an anti-IL-17 autoantibody and/or (ii) the level of an [IL-17/anti-IL-17 autoantibody] complex may be carried out according to one of the following methods: immunoelectrophoresis, counterelectrophoresis, gel immunodiffusion, immunoagglutination, immunofluorescence, ELISA, nephelometry and immunoblotting.

According to one embodiment, step a) is carried out in the form of an ELISA assay. Immunological quantification tests in the form of ELISA assays are known to those skilled in the art. They may in particular be carried out in the form of competitive ELISAs (see examples and FIG. 1A) or of indirect ELISAs (see FIG. 1B).

According to one subembodiment, a competitive ELISA assay may be carried out for determining the level of an anti-IL-17 autoantibody in a sample.

According to one subembodiment, an indirect ELISA assay may be carried out for determining the level of an [IL-17/anti-IL-17 autoantibody] complex in a sample.

Thus, a competitive ELISA assay for determining the level of an anti-IL-17 autoantibody in a sample may comprise the following steps:

a) optionally bringing a sample which may contain an anti-IL-17 autoantibody into contact, in the presence of an agent capable of inhibiting the interaction of rheumatoid factor possibly present, with said autoantibodies (for example a serum from another organism);

b) bringing said sample into contact with an interleukin IL-17 for a period of time sufficient for said anti-IL-17 autoantibodies to interact with said interleukin;

c) bringing said sample into contact with an exogenous antibody directed against said interleukin for a period of time sufficient for said exogenous antibody to compete with said anti-IL-17 autoantibodies for interaction with said interleukin;

d) determining the level of anti-IL-17 autoantibody in said sample on the basis of the level of exogenous antibody interacting with said interleukin.

In particular, said exogenous antibody may be in labeled form, in order to facilitate the determination of the level of autoantibody in step d).

Step d) may also include a step of binding said biological sample to a support on which anti-IL-17 antibodies are bound.

An indirect ELISA assay for determining the level of an [IL-17/anti-IL-17 autoantibody] complex in a sample may comprise the following steps:

a) bringing a sample which may contain an [IL-17/anti-IL-17 autoantibody] complex into contact with a support on which anti-IL-17 antibodies are bound, for a period of time sufficient for said complexes to interact with said antibody;

b) bringing said sample into contact with an exogenous antibody directed against said anti-IL-17 autoantibody, for a period of time sufficient for said exogenous antibody to interact with said anti-IL-17 autoantibody;

c) determining the level of [IL-17/anti-IL-17 autoantibody] complex in said sample on the basis of the level of exogenous antibody interacting with said autoantibody.

In particular, said exogenous antibody may be in labeled form, in order to facilitate the determination of the level.

Said samples may most particularly be blood or blood-derived samples, such as plasma or serum.

According to one embodiment, an in vitro method according to the invention may also comprise a step of determining, in a biological sample from said individual, the level of a polypeptide chosen from: the cytokines IL-17A, IL-17F, IL-25, IL-23, transcription factors, including RORγt, and IL-17 interleukin receptors such as IL-17RA, IL-17RB or IL-17RC, and the autoantibodies.

Thus, according to one particular embodiment, an in vitro method according to the invention may comprise a step of determining, in a biological sample from said individual, the level of a polypeptide chosen from: the cytokines IL-17A, IL-17F, IL-25, IL-23, the transcription factor RORγt, and the IL-17RA, IL-17RB, IL-17RC receptors, autoantibodies directed against IL-1α, autoantibodies directed against IL-8 and/or autoantibodies directed against osteopontin.

Pharmaceutical Composition and Therapeutic Applications

Anti-IL-17 antibodies as such, and for the treatment or prevention of chronic autoimmune or inflammatory diseases, are described below.

These anti-IL-17 antibodies may be used as medicaments, or else used for the preparation of a medicament.

The demonstration of anti-IL-17 autoantibodies and of [IL-17/anti-IL-17 autoantibody] complexes in patients suffering from destructive and non-destructive rheumatoid arthritis also makes it possible to envision the administration of anti-IL-17 antibodies to particular subgroups of individuals suffering from:

destructive rheumatoid arthritis;

non-destructive rheumatoid arthritis;

rheumatoid arthritis associated with anti-IL-17 autoantibody production;

rheumatoid arthritis not associated with anti-IL-17 anti-IL-17 autoantibody production; and/or bone destruction associated with any one of the preceding subgroups.

Thus, the present invention relates to an isolated anti-IL-17 antibody for the treatment or prevention (i) of destructive rheumatoid arthritis and/or (ii) of non-destructive rheumatoid arthritis and/or (iii) of rheumatoid arthritis in an individual producing anti-IL-17 autoantibodies and/or (iv) of rheumatoid arthritis in an individual not producing anti-IL-17 autoantibodies, and/or (v) of bone destruction associated with any one of groups (i) to (iv).

The present invention also relates to the use of an isolated anti-IL-17 antibody for preparing a medicament for the treatment or prevention (i) of destructive rheumatoid arthritis and/or (ii) of non-destructive rheumatoid arthritis and/or (iii) of rheumatoid arthritis in an individual producing anti-IL-17 autoantibodies and/or (iv) of rheumatoid arthritis in an individual not producing anti-IL-17 autoantibodies, and/or (v) of bone destruction associated with any one of groups (i) to (iv).

Preferably, the subgroups of individuals to be taken into consideration in the context of an administration of anti-IL-17 antibodies and/or of the preparation of a medicament are those suffering from:

destructive rheumatoid arthritis;

rheumatoid arthritis not associated with anti-IL-17 autoantibody production; and/or bone destruction associated with any one of the preceding subgroups.

Said subgroups of individuals may in particular be those evaluated by any one of the in vitro evaluation methods according to the invention.

Said anti-IL-17 antibodies according to the invention may in particular be those selected by any one of the in vitro selection methods according to the invention.

An anti-IL-17 antibody according to the invention may be an anti-IL1-7 antibody obtained from a biological sample from an individual producing anti-IL-17 autoantibodies.

In particular, said anti-IL-17 antibody is an isolated human anti-IL-17 antibody obtained from a biological sample from an individual producing anti-IL-17 autoantibodies.

An anti-IL-17 antibody may also be derived from a cell producing anti-IL-17 autoantibodies; said producer cell (for example a B lymphocyte and/or a hybridoma) being obtained from a biological sample from an individual producing said anti-IL-17 autoantibodies.

According to one embodiment, said individual from which said anti-IL-17 autoantibody or said producer cell is isolated is suffering from rheumatoid arthritis.

According to one embodiment, the anti-IL-17 antibody is an isolated human anti-IL-17 antibody obtained from a biological sample from an individual producing anti-IL-17 autoantibodies.

According to one embodiment, the anti-IL-17 antibody is an isolated human anti-IL-17 antibody obtained from a biological sample from an individual suffering from rheumatoid arthritis and producing anti-IL-17 autoantibodies.

According to one exemplified embodiment, the anti-IL-17 antibody is a human antibody directed against human interleukin IL-17 obtained after immortalization of human B lymphocytes from PBMCs ("Peripheral blood mononuclear cells") from individuals suffering from rheumatoid arthritis and producing anti-IL-17 autoantibodies.

Preferably, said anti-IL-17 antibodies are monoclonal antibodies.

The anti-IL-17 antibody may be a human antibody directed against human interleukin (IL-17A) or human interleukin IL-17F, or directed against both human IL-17A and human IL-17F.

According to one preferred embodiment, the anti-IL-17 antibody is an anti-IL-17A antibody.

Such an antibody may be identical or substantially identical to a natural antibody, for example produced from antibody-producing cells, such as B lymphocytes from individuals suffering from rheumatoid arthritis, such as individuals suffering from non-destructive rheumatoid arthritis and/or from rheumatoid arthritis associated with anti-IL-17 autoantibody production.

Thus, the anti-IL-17 autoantibody may preferably be a human autoantibody directed against human interleukin IL-17A or human interleukin IL-17F, or directed against both human IL-17A and human IL-17F.

An isolated anti-IL-17 antibody as defined above may be used in a pharmaceutical composition and/or as a medicament.

The invention therefore also relates to a pharmaceutical composition or a medicament comprising said anti-IL-17 antibody.

EXAMPLES

Materials and Methods

Patients: 60 patients suffering from rheumatoid arthritis (RA) were selected from a wide database, and classified in two groups according to a 1:1 ratio, on the basis of their radiographic degree of destruction (Larsen score). Destructive rheumatoid arthritis (RA) is defined by a wrist Larsen score greater than 2, and non-destructive RA by a wrist Larsen score between 0 and 1. All the parameters relating to RA were obtained from the clinical database. The destructive and non-destructive RA patients were paired according to sex (female/male=21/09 vs. 20/10), age (66.1±10.8 vs. 71.3±9.3 years old), disease duration (18.6±9.6 vs. 23.0±9.8 years), DAS28 (3.9±1.2 vs. 4.0±1.4), with the exception of the Larsen score (0.5±0.5 vs. 3.3±1.0, p<0.0001) (table 1). Thirty healthy donors were used as negative controls. Written consent was obtained from each subject. The protocol is in accordance with the ethics committee of the hospitals of Lyon.

Detection of anti-IL-17 antibodies by a competitive ELISA assay (FIG. 1A): the plasma of RA patients and of healthy donors is first preincubated with horse serum overnight in order to prevent cross-reactions with rheumatoid factor (RF). Plasma samples at 1/4, 1/8 and 1/16 dilutions are then incubated with 30 μl of IL-17A (50 ng/ml) (IL17A, Dendritics, Lyon, France). After incubation for 1 h, an anti-human IL-17 detection antibody (406G9.02-HRP, Dendritics, Lyon, France) was added. This mixture is transferred into a 96-well plate comprising a mouse anti-human IL-17 antibody (408H6.01, Dendritics, Lyon, France) for 2 h. The tetramethylbenzidine (TMB) substrate was added and the absorbance at 620 nm is determined.

Detection of IL-17/anti-IL-17 antibody complexes by an indirect ELISA assay (FIG. 1B): the wells are incubated overnight with 3 μg/ml of an anti-IL-17 capture antibody (408H6.01). After washing with PBS/0.05% Tween, 100 μl of plasma diluted to 1/4 are added overnight (first dilution to 1/2 in horse serum and second dilution in a PBS/BSA/Tween mixture). After 3 washes, a goat anti-human IgG Fc fragment antibody (anti-human-IgG Fc) conjugated to peroxidase (109-035-098, Jackson Immuno Research, Baltimore, USA) at $1/5000^{th}$ is added and incubated for 1 h 30. As a positive control, a mixture of a human anti-human IL-17A antibody isolated from the blood of a patient suffering from rheumatoid arthritis (5 μg/ml) and an interleukin IL-17 at 500 ng/ml was used. This human antibody directed against human interleukin IL-17 was obtained after immortalization of human B lymphocytes from PBMCs of patients suffering from rheumatoid arthritis and after immortalization with EBV and the CD40 system (DDXK-HuBBB, Dendritics, Lyon, France). In order to verify the elimination of rheumatoid factor, the reaction was tested with and without horse serum.

Statistical analysis: the data were expressed as mean±SD. A non-parametric two-sided test (t-test) of the Graphpad Prism software was used. A p value of less than 0.05 is considered to be statistically significant.

Example 1—High Incidence of Anti-IL-17 Autoantibodies in Patients Suffering from Non-Destructive Rheumatoid Arthritis A competitive ELISA assay was developed for measuring the anti-IL-17 autoantibodies in the plasma. In order to prevent cross-reactivity with the rheumatoid factor present in large amounts in the plasma, a step of preincubation in the presence of horse serum was added. A positive control test using purified anti-IL-17 antibodies showed a decrease in absorbance with the dilution (FIG. 1A), whereas nonspecific antibodies showed no variation.

The plasma from 30 healthy donors made it possible to identify a threshold value. An absorbance at 0.9±0.1 for a 1/2 dilution, and no variation for dilutions from 1/4 to 1/8, were observed, which indicates an absence of positivity to the anti-IL-17 autoantibodies.

Conversely, anti-IL-17 antibodies were detected for 36.6% of the 60 patients suffering from rheumatoid arthritis (p<0.05 vs. controls), which indicates a link between the presence of autoantibodies directed against interleukin IL-17 and rheumatoid arthritis.

In order to study the relationship between the severity of rheumatoid arthritis, plasmas from individuals suffering from destructive and non-destructive rheumatoid arthritis. The various groups are paired, as indicated in the Materials & Methods section (see table 1 below). The "non-destructive" patients had exhibited this pathological condition for several years, so as to confirm the reduced severity.

TABLE 1

Clinical parameters of healthy donors and of destructive and non-destructive rheumatoid arthritis patients, and incidence of anti-IL-17 autoantibodies

| Parameters | Healthy donors (n = 30) | RA patients (n = 60) | Non-destructive (n = 30) | Destructive (n = 30) | p value |
|---|---|---|---|---|---|
| Sex (F:M) | 20:10 | 41:19 | 21:09 | 20:10 | n.s |
| Age (years) | 60.0 ± 5.5 | 68.7 ± 10.5 | 66.1 ± 10.8 | 71.3 ± 9.3 | n.s |
| Disease duration (years) | | 20.8 ± 9.7 | 18.6 ± 9.6 | 23.0 ± 9.8 | n.s |
| DAS28 | | 4.0 ± 1.3 | 3.9 ± 1.2 | 4.0 ± 1.4 | n.s |
| Larsen score | | 1.9 ± 0.8 | 0.5 ± 0.5 | 3.3 ± 1.0 | <0.0001 |
| Rheumatoid factor positive (%) | | 63.2 | 57.1 | 69.2 | n.s |
| Anti-CCP antibody positive (%) | | 58.3 | 50.0 | 66.6 | n.s |
| Anti-IL-17 antibodies (%) | 0.0 | 35.4 | 46.6 | 24.2 | <0.05 | n.s = not significant,
F = female,
M = male,
Abs = antibodies,
DAS28 = Disease Activity Score 28.

The anti-IL-17 antibodies were detected in 46.6% of "non-destructive" patients, whereas these antibodies were detected only in 24.2% of "destructive" patients. These results suggest that natural anti-IL-17 autoantibodies are associated with rheumatoid arthritis which has a better prognosis, regarding bone destruction.

Similar observations were reported for other cytokines. In particular, increased levels of autoantibodies directed against IL-1α in patients suffering from rheumatoid arthritis suggest a protective role of these anti-IL-1α antibodies with regard to bone destruction.

Conversely, autoantibodies directed against IL-8 and osteopontin were associated with extra-articular manifestations of rheumatoid arthritis.

The invention claimed is:

1. An in vitro method for isolating an anti-IL-17A autoantibody or a cell producing the autoantibody comprising:
   a) selecting an individual with a non-destructive rheumatoid arthritis;
   b) detecting an anti-IL-17A autoantibody and/or an IL-17A/anti-IL-17A autoantibody complex, or a cell producing the autoantibody in a biological sample from the individual; and
   c) isolating the anti-IL-17A autoantibody or the cell producing the autoantibody from the biological sample of the individual.

2. The in vitro method as claimed in claim 1, wherein the method comprises step c) isolating the cell producing the anti-IL-17A autoantibody from the biological sample of the individual.

3. The in vitro method as claimed in claim 1, wherein the method comprises step b) detecting an IL-17A/anti-IL-17A autoantibody complex in a biological sample from the individual, and step c) isolating the anti-IL-17A autoantibody from the biological sample of the individual; or wherein the method comprises step b) detecting a cell producing the anti-IL-17A autoantibody in a biological sample from the individual; and c) isolating the cell producing the autoantibody from the biological sample of the individual.

4. The in vitro method as claimed in claim 1, wherein the anti-IL-17A autoantibody inhibits the IL-17A activity, and can be used for treating psoriasis, multiple sclerosis, Crohn's disease, vasculitis, myositis, hepatitis, inflammatory and autoimmune nephropathy, neutrophilic dermatosis, Verneuil's disease, uveitis, and a bone destruction associated with a chronic autoimmune or inflammatory disease selected from: rheumatoid arthritis, psoriatic arthritis, and ankylosing spondylitis.

5. The in vitro method as claimed in claim 4, wherein the method comprises step b) detecting an anti-IL-17A autoantibody in a biological sample from the individual.

\* \* \* \* \*